(12) United States Patent
Muenzer

(10) Patent No.: US 9,957,181 B2
(45) Date of Patent: May 1, 2018

(54) PASTEURIZATION SYSTEM WITH PURIFICATION OF THE PROCESS LIQUID

(71) Applicant: KRONES AG, Neutraubling (DE)

(72) Inventor: Jan Muenzer, Harrislee (DE)

(73) Assignee: KRONES AG, Neutraubling (DE)

(*) Notice: Subject to any disclaimer, the term of this patent is extended or adjusted under 35 U.S.C. 154(b) by 365 days.

(21) Appl. No.: 14/743,343

(22) Filed: Jun. 18, 2015

(65) Prior Publication Data
US 2015/0368135 A1    Dec. 24, 2015

(30) Foreign Application Priority Data

Jun. 24, 2014 (DE) .......... 10 2014 108 798

(51) Int. Cl.
*C02F 1/00* (2006.01)
*C02F 9/00* (2006.01)
(Continued)

(52) U.S. Cl.
CPC ............. *C02F 9/00* (2013.01); *A23L 3/04* (2013.01); *A61L 2/10* (2013.01); *A61L 2/22* (2013.01);
(Continued)

(58) Field of Classification Search
CPC ............ B01D 21/0006; B01D 21/0012; B01D 21/0018; B01D 21/0021; B01D 21/0024;
(Continued)

(56) References Cited

U.S. PATENT DOCUMENTS 2,282,187 A * 5/1942 Herold ............... A23L 3/04
426/407
3,104,672 A * 9/1963 Holdren ............... B08B 9/093
134/168 R
(Continued)

FOREIGN PATENT DOCUMENTS

CN     103086021 A    5/2013
CN     103768622 A    5/2014
(Continued)

OTHER PUBLICATIONS

Extended European Search Report for application No. 15172842.5, dated Mar. 9, 2016.
(Continued)

*Primary Examiner* — Pranav N Patel
(74) *Attorney, Agent, or Firm* — Marshall, Gerstein & Borun LLP

(57) ABSTRACT

Pasteurization system with purification of the process liquid, with a feed and evacuation conveyor system for containers. At least one treatment zone with sprinkling nozzles to spray the containers with a process liquid such as water, the treatment zone including a screening unit with a sedimentation area for the deposition of sediment from the process liquid, a closed-loop circuit to re-use the process liquid, with devices to remove the sediment from the sedimentation area for each zone and to feed the sediment into a central filter unit. The central filter unit has at least one filter module for the filtration of solid matter from the inputted sediment so that the filtered process liquid is conserved. Devices to (Continued)

return the filtered process liquid to one or several treatment zones are also provided.

15 Claims, 4 Drawing Sheets

(51) Int. Cl.
| | |
|---|---|
| *B01D 29/50* | (2006.01) |
| *A23L 3/04* | (2006.01) |
| *A61L 2/10* | (2006.01) |
| *A61L 2/22* | (2006.01) |
| *B01D 21/00* | (2006.01) |
| *C02F 1/50* | (2006.01) |
| *C02F 1/32* | (2006.01) |
| *C02F 1/44* | (2006.01) |
| *B01D 21/24* | (2006.01) |

(52) U.S. Cl.
CPC ....... *B01D 21/009* (2013.01); *B01D 21/0045* (2013.01); *B01D 29/50* (2013.01); *C02F 1/008* (2013.01); *B01D 21/2488* (2013.01); *C02F 1/325* (2013.01); *C02F 1/441* (2013.01); *C02F 1/442* (2013.01); *C02F 1/444* (2013.01); *C02F 1/50* (2013.01); *C02F 2201/002* (2013.01); *C02F 2209/02* (2013.01); *C02F 2301/046* (2013.01); *C02F 2303/04* (2013.01)

(58) Field of Classification Search
CPC ............ B01D 21/0039; B01D 21/0045; B01D 21/0048; B01D 2311/04; B01D 2311/10; B01D 2311/103; B01D 2311/12; B01D 2311/2619; B01D 2311/2649; C02F 1/44; C02F 1/441; C02F 1/442; C02F 1/444; C02F 1/32; C02F 1/50; C02F 2103/32; C02F 2209/02; C02F 2301/046
See application file for complete search history.

(56) References Cited

U.S. PATENT DOCUMENTS

| | | | | |
|---|---|---|---|---|
| 3,732,917 A | * | 5/1973 | Deubel | .................. B65B 63/08 134/68 |
| 4,351,733 A | * | 9/1982 | Salzer | ................ B01D 21/0042 210/319 |
| 4,441,406 A | * | 4/1984 | Becker | .................... A23L 3/003 422/25 |
| 4,704,958 A | | 11/1987 | Braymand | |
| 2009/0280222 A1 | | 11/2009 | Nielsen et al. | |
| 2009/0324790 A1 | * | 12/2009 | Hilgren | .................. A22B 7/008 426/335 |
| 2010/0154828 A1 | * | 6/2010 | Green | ...................... B08B 9/08 134/21 |
| 2010/0186347 A1 | * | 7/2010 | Munzer | ..................... A23L 3/02 53/127 |
| 2012/0138531 A1 | * | 6/2012 | Oliveros | ................. C02F 1/325 210/638 |
| 2012/0312419 A1 | | 12/2012 | Wagner et al. | |
| 2014/0110360 A1 | | 4/2014 | Braun et al. | |

FOREIGN PATENT DOCUMENTS

| | | |
|---|---|---|
| CN | 103796921 A | 5/2014 |
| DE | 102005028195 A1 | 12/2006 |
| DE | 102011077375 A1 | 12/2012 |
| DE | 102012219184 A1 | 5/2014 |
| EP | 1043033 A1 | 10/2000 |
| EP | 2505505 A2 | 10/2012 |
| EP | 2722089 A1 | 4/2014 |
| WO | WO-2006079541 A2 | 8/2006 |
| WO | WO-2010015369 A1 | 2/2010 |
| WO | WO-2013029856 | 3/2013 |
| WO | WO-2015090914 A1 | 6/2015 |

OTHER PUBLICATIONS

Search Report for European Application No. EP 15 17 2842, dated Oct. 27, 2015.
German Search Report for Application No. 102014108798.4, dated Oct. 6, 2014.
Notification of the First Office Action, The State Intellectual Property Office of the People's Republic of China, Application No. 201510472974.4, dated Jan. 3, 2017.
English Translation of a Chinese Notification of the Second Office Action for Application No. 201510472974.4, dated Sep. 14, 2017.

\* cited by examiner

PASTEURIZATION SYSTEM WITH PURIFICATION OF THE PROCESS LIQUID

CROSS-REFERENCE TO RELATED APPLICATION

The present application claims priority to German Application No. 102014108798.4, filed Jun. 24, 2014. The priority application, DE 102014108798.4, is hereby incorporated by reference.

FIELD OF THE INVENTION

The present invention relates to a pasteurization system with purification of the process liquid.

BACKGROUND OF THE INVENTION

Devices for thermal treatment of products that are filled into containers, for example bottles, PET containers or cans, are known in the state of the art. These devices may comprise, for example, pasteurization systems, heat- or cooling devices. Also, these devices frequently appear in combination with multi-zone pasteurization systems in order to bring the products at least temporally on different, defined temperature levels. The heat exchange generally occurs through spraying with a process liquid such as water. Spraying shall be understood as sprinkling or irrigation of the containers. The water used in the process, which is also referred to as process water, is typically drizzled through nozzles above the product flow. The process water thereby releases heat to the product or absorbs heat due to the temperature difference. The used water is usually re-used, at least in part. There is a circulation mode for the process water.

In the process, contamination may occur in different ways in the pasteurization system, which may significantly impair the sprinkling system and eventually the functioning of the pasteurization system. For example, a biofilm may develop in parts of the system or in individual zones of that system. Biofilms consist, for instance, of a mucus layer (a film) in which microorganisms, such as bacteria, algae, fungi, etc., may be embedded.

Screening bands are typically used to eliminate particles, such as glass shards, sand and/or settling sediments from the process water. A screening band extending over several zones, as is used in many cases, has the disadvantage of requiring a horizontal band guiding system, so that the essentially vertical water flow accordingly leads to an extension of the machine height. This excess height may, for example, amount to 400 mm and constitute significant additional expenses in the area of the conveyor systems to feed and evacuate the containers. In case of a screening process per zone by respectively one screening band, the arising screening costs are disproportionally high. Plug-in screens are also used in simpler machines.

Both types of screens have the unfavorable effect of being obstructed for example by suspended sediments, mucilage and substances floating on the water. The mentioned materials stay, for example, on the screen surfaces where they accumulate. There, these substances increasingly hamper the throughput of the screens. Hence, the screens must be checked regularly for obstructions and cleaned. Especially if plug-in screens are used, the plug-in screens must, if appropriate, be pulled out and cleaned, meaning that the systems with plug-in screens lead to a high workload and/or staffing expenses. Typically, there are also attempts to dissolve suspended sediments, mucilage and substances floating on the water through chemical treatment. If, however, dissolving materials such as mucilage or similar substances through chemical treatment is not possible, or if there is a defect in the chemical water treatment process, the screen surfaces of the mentioned screen types will clog even more quickly.

The mesh size of a screen limits the attainable throughput rate. Typically, particles with a maximum size of 2-3 mm may be filtered with a band screen or a plug-in screen. Needle-shaped glass shards might still be able to pass such meshes, which may subsequently obstruct the nozzles for the sprinkling process. Furthermore, the nozzles as well as pump impellers are often made of plastic. Shards and other solid materials with a diameter smaller than 2-3 mm, however, may obstruct plastic nozzles from inside. A regular replacement of the nozzles is just as undesired as uncontrolled sprinkling due to ragged or lacerated nozzles, though. If, however, fresh water is used for the internal cleaning process, only cold water will be available in many cases. As the water used for purification is usually lost, there are additional water consumption costs. Also, cold water does not have the same cleaning power as warm water. A higher sprinkling pressure is consequently required for cold water. If the water from the sprinkling circuit is used, the removed dirt will accumulate in the plug-in screens and must be extracted manually at a later time. When the sprinkling processes are run, cleaning the areas below the water level is complicated due to the required water level in the respective zone of the system. To clean such an area, it is often required to let collected water flow away and then to manually clean these areas. In that case, however, fresh water with a high pressure is needed to be able to remove biofilms from the walls that are located under the water level. Hence, working hours, water and energy are needed to a large extent to clean this area. If, for example, biocide is dispensed in the deposit of a zone, the biocide is sucked up with the process water by the sprinkling water pump and drizzled over the areas to be cleaned. Areas that remain unsprayed by the sprinkling system or the treatment chamber above the sprinkling pipes are often heavily contaminated by a biofilm. After a cleaning process in which these areas are not reached sufficiently, these areas may lead to a repeated germ contamination of the pasteurizer. Then, they need to be cleaned again and possibly with extensive manual effort. The thermal sanitation process, which is often used, requires a considerable amount of thermal energy, especially to heat up practically the entire system and to bring all zones to the sanitation temperature. Hence, this entails a substantial expenditure of time beyond the production. Heating and action often require several hours. Typically, the pasteurization water shall be evacuated before. Consequently, sanitation requires the replacement of practically the whole water content of the system. Such filling and evacuation processes also require additional operating time and water consumption. Hence, this procedure is extremely costly for the operator in every respect.

In view of the problems cited above, the purpose of the present invention consists of providing a pasteurization system with purification of the process liquid, whereby the hygiene inside the system during treatment of the containers is improved and whereby a lower obstruction risk for the system is achieved so that the system becomes more efficient.

DESCRIPTION OF THE INVENTION

According to the invention, there is provided a pasteurization system with purification of the process liquid, with a feed and evacuation conveyor system for containers; with at least one treatment zone with sprinkling nozzles to spray the containers with a process liquid such as water, whereby the treatment zone comprises a screening unit with a sedimentation area for the deposition of sediment from the process liquid; and with a closed-loop circuit to re-use the process liquid; as well as devices to remove the sediment from the sedimentation area for each zone and to feed the sediment into a central filter unit, whereby the central filter unit comprises at least one filter module to filter solid materials out of the fed sediment, so that the filtered process liquid is conserved; and devices to return the filtered process liquid to one or several treatment zones.

The containers are closed. The treatment of the containers occurs through sprinkling or spraying from outside. The screening unit uses the gravity sedimentation especially for small particles and settling sediments that are carried along by the process liquid, typically the process water. These particles have a higher density than the process liquid and settle on the floor of the screening unit as sediment. The process liquid is led into a circulation loop and typically re-used. For one or several of the treatment zones, the sediment may be pulled off the floor of the treatment floor by means of a removal unit and fed into a central filter unit. It is clear that a mixture of sediment and process liquid is removed in this process, which is referred to as sediment for the purpose of simplification. Not only settled solids are removed. The sediment is fed into the central filter unit and filtered there. Therefore, the central filter unit comprises, for example, at least a filter module to filter solid materials out of the sediment. Through this process, a filtered process liquid may be obtained. The process liquid filtered this way may consequently be rid of solid materials to a large extent. The filtered process liquid may either be returned to the zone from which it has been taken or it is also possible to return the filtered process liquid within the system to one or several other zones.

In the system, the devices for sediment removal for each zone may be developed as part of the sedimentation area and create a vortex flow in a way that the sediment may be pulled out of the sedimentation area.

The central filter unit in the system may comprise a further filter module to filter suspended matter.

Biofilms may develop especially under certain environmental conditions or in case of sufficient heat in the process water. The temperatures in some treatment zones are just ideal for the growth of biofilms. Through a further filter module of this type, suspended matter such as detached biofilm and mucilage may be filtered out of the sediment.

In the system, the central filter unit may comprise a further filter module, which is developed to implement microfiltration and/or ultrafiltration and/or nanofiltration and/or reverse osmosis filtration processes.

Sometimes, nutrients may suddenly be added to the process liquid in a relatively high concentration, for example through leaking or burst containers so that their content is mixed with the process liquid in the respective zones. Such a filter module may filter out nutrients in the process liquid. Thereby, different sizes and/or types of nutrients may be removed from the process liquid by means of different membrane sizes.

The central filter unit in the system may comprise another filter module to irradiate the filtered process liquid with UV radiation.

A further step to improve the hygiene is a UV radiation of the filtered process liquid. This occurs typically after having filtered out solid matter and/or suspended matter and/or nutrients. The filtered process liquid may be sanitized through irradiation with UV light. Sanitation is desirable as it may reduce the new development of a biofilm in the filtered process water that is returned to the treatment zones.

The system may comprise a dosage unit that is developed to add biocide to the process liquid filtered by the central filter unit. A further, especially complementary sanitation possibility is the addition of biocide to the filtered process liquid. Thereby, the number of germs in the filtered process liquid may be further reduced. Hence, the filtered process liquid is sanitized even better and the repeated development of germs and biofilms is inhibited even more effectively.

One or more or all treatment zones in the system may comprise respectively one internal purification module with one or several nozzle systems, which are developed to clean one or more internal areas of the treatment zones with filtered process liquid.

The filtered and typically sanitized process liquid may be used for the internal purification of the treatment zones. As filtered process liquid, typically process water, is significantly clearer and more sanitized, it may especially be used for cleaning purposes as well. Additional fresh water consumption may be essentially reduced or completely avoided as the filtered and sanitized process water is used for the internal purification.

At least one of the nozzle units in the system may be developed to spray the ceiling above the sprinkling nozzles with filtered process liquid.

So-called sprinkling or drizzling shadows often develop above the sprinkling nozzles that are used for the treatment of the containers in the respective treatment zone. Sprinkling shadows are areas that, although they are wetted with condensation water and/or liquid, are not regularly sprayed and are therefore particularly susceptible to the development of biofilms. With a nozzle system that targets these areas, they may be cleaned systematically with the process water.

In the system, the containers to be sprinkled in the treatment zones may be guided on several conveyor systems arranged on top of each other, and at least one of the nozzle units may be installed between two conveyor systems arranged on top of each other in a way that areas arranged between the conveyor systems may be cleaned.

At least one of the nozzle units in the system may be arranged in a way that areas, which are located under the water level during operation of the system, may be rinsed.

Areas of the zones that are under the water level of a treatment zone during normal operation are often difficult to clean. Also here, biofilms develop on the lateral walls. If the collected water is evacuated in a treatment zone, these areas will become vacant. These areas may subsequently also be rinsed by means of nozzle systems. In addition, such nozzle systems may be designed in a way that they already enable rinsing of the lateral walls under the water level whereby biofilms and contamination of the lateral walls may be further reduced.

The nozzle units in the system may comprise rotational nozzles that are installed rotatably by 360°.

By means of rotational nozzles, all surrounding areas may be sprayed particularly well.

The system may further comprise a control unit that is designed in a way to control devices for sediment evacuation from the sedimentation area for each zone and for feeding of the sediment into the central filter unit.

In the system, the control unit may be designed to measure the temperature of the process liquid of the treatment zones and to use filtered process liquid from at least one treatment zone with a higher temperature of the process liquid for internal purification of a treatment zone with a colder process liquid.

The control unit may control valves and hence the feeding and evacuation of process liquid in and from the treatment zones. Equally, the control unit may communicate with temperature sensors that may measure the temperature of the process liquid and/or the internal temperature of a treatment zone. Hence, the control unit may regulate whether and, if appropriate, from which treatment zone warmer process liquid is withdrawn, filtered and sanitized in order to be subsequently re-used in a colder treatment zone, especially for internal cleaning.

In the system, the screening unit in the treatment zone may further comprise a pump and an inclined blade purifier with several slant, parallel blades installed under the liquid surface, whereby the pump pumps the process liquid alongside the blades.

The pump in the system may pump the process liquid over the deepest point of a treatment zone so that sediment may be deposited.

In the screening units of the treatment zones, a filter unit developed as an inclined blade purifier may be installed for all or at least some screening units. Hence, it is an additional zone-related filter unit. The process liquid is pumped through the screening unit, for example by means of a pump. The blades may thereby provide a large sedimentation area in a compact form where the process liquid is flowing past. At the blades, i.e. at the sedimentation areas, the particles may sediment and this sediment may sink down to the bottom of the screening unit due to the gravitational force. It is clear that the pump performance may be chosen in a way that the sinking particles be not carried away by a current. The blades may be completely wetted, i.e. they are to be dipped in the liquid. Therefore, contamination of the blade surfaces may be considerably reduced and the blades remain practically free of residues. Hence, residues cannot dry on the blades either. Due to their surface properties, the blades may act as additional sedimentation areas. The porosity of the surface of the blades may thereby be kept as low as possible. Through this process, the accumulation of organic suspended matter such as mucilage on the blades may also be significantly reduced or even eliminated. Even if such substances accumulated to a limited extent on the surfaces of the blades, they would practically not disturb any of the sedimentation properties of the blades. Consequently, the blades could support the deposition of sediment that could then accumulate at the bottom of the screening unit. Hence, the efficiency of the system may be further increased.

Therefore: the invention described in this document allows for a filtration of the process liquid of a pasteurization system and a re-use of the filtered process liquid. As the sediment is removed, sediment and suspended matter and/or dissolved nutrients may be removed from the process liquid by means of the central filter unit and hence the process liquid may be kept very clean. This leads to an increased lifetime of the system. Also needle-shaped particles, shards, etc., that could pass through a plug-in screen or a filter band of the pasteurizer in conventional systems, may be collected in the sedimentation process and filtered out by means of the central filter unit. Through this process, obstructions or damages of sprinkling nozzles may be avoided to the greatest possible extent. The invention especially allows for an internal purification of treatment zones of the system, practically without any additional fresh water consumption. The internal purification may occur, for example, during operation of the system. An improper mix of the temperatures may be practically ruled out by the control of the closed-loop system. The dirt that is separated from the areas during cleaning may be filtered out by the central filter system through the closed-loop of the process liquid and finally be removed. Through the addition of biocide to the filtered process liquid, the cleaning nozzles may bring the biocide to areas where it does normally not arrive. The cleaning with UV radiation may also have a biocidal effect as UV radiation creates free radicals that, in turn, may have a biocidal effect. Through the addition of these free radicals to the internal cleaning process, these free radicals may be supplied directly to the areas to be cleaned. Therefore, the consumption of sanitation chemicals may be reduced. For the cleaning of areas under the water level, hot water from the respective pasteurization zones may be used after emptying the treatment zones. Hence, thermal energy may be saved. Traditionally, the system would have to be heated up in certain zones, sections or even completely in order to sanitize them thermally. Operating costs for water, electricity and working hours, which arise as a result of the forced production downtime, could therefore be reduced. Maintenance intervals could be extended or even omitted completely in some cases.

The following part describes design variants of the invention under reference to the drawings. The described design variants shall, in every respect, be regarded as merely illustrative and not restrictive, and different combinations of the mentioned characteristics are included in the invention.

SHORT DESCRIPTION OF THE FIGURES

DETAILED DESCRIPTION

Figure 1:
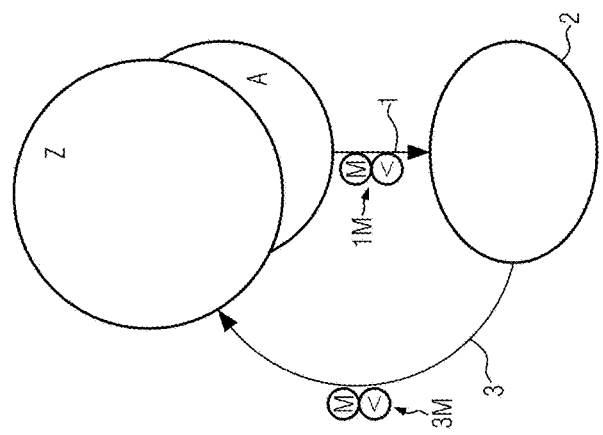
FIG. 1 shows a schematic sketch of a pasteurization system according to the present invention.
Figure 4:
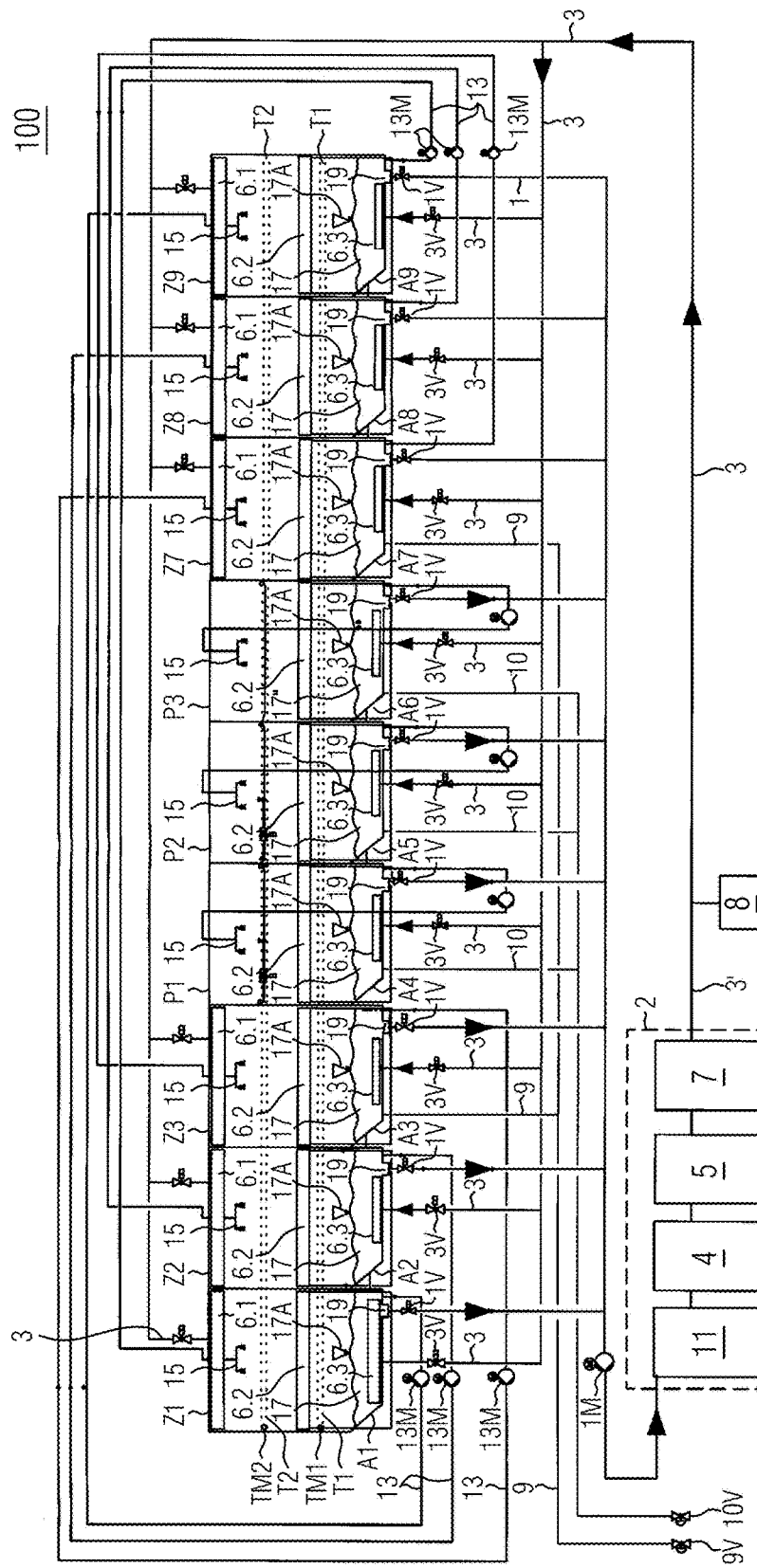
FIG. 4 shows a pasteurization system with several treatment zones that is equivalent to the pasteurization system from FIG. 3.

FIG. 1 shows a schematic sketch of a pasteurization system according to the present invention. An area with at least one treatment zone Z is installed for the treatment of liquids filled in containers. The containers are closed. Typically, the containers are sprayed with process liquid, especially with process water. Details are shown in FIG. 4. The containers are not explicitly shown in FIG. 1. During the treatment of the containers, dirt or particles may detach from the containers while the containers are being sprayed. In the pasteurization system from FIG. 1, there is a screening unit A for screening or deposition of sediment from the process liquid. The screening system A typically comprises a screen box or deposition box; see FIG. 4. The pasteurization system comprises devices 1 to remove the sediment, in this case a pipeline 1 with a pump 1M. By means of the pump 1M, the sediment is removed from the screen box and led into a central filter unit 2. The central filter unit 2 comprises at least one filter module for the filtration of solid materials, see FIG. 4. For example, the filter module of the central filter unit may comprise a gap filter with a defined gap size. The gap size may, for instance, amount to 40-60 μm. But other gap sizes are also possible. Particles that are retained in this filter module may be detached from the filter module through reverse rinsing, for example by means of pneumatic reverse rinsing. Therefore, the filter module of the filter unit 2 may be cleaned by means of a pneumatic reversing stroke and be used several times. The central filter unit 2 of FIG. 1 may further contain filter modules that are explained on the basis of FIG. 4. The central filter unit may especially contain a UV module for the irradiation of the filtered process liquid, whereby bacteria and fungi may be cauterized.

FIG. 1 further shows devices 3, for example a pipeline 3 with a pump 3M to return the filtered process water to the treatment zone Z. Hence, the filtered process water may be used again in the treatment zone Z in a filtered, i.e. purified, way. Hence, there is an essentially closed loop for the process water, whereby "closed loop" shall be understood in the sense that no fresh water needs to be supplied in addition.

Figure 2:
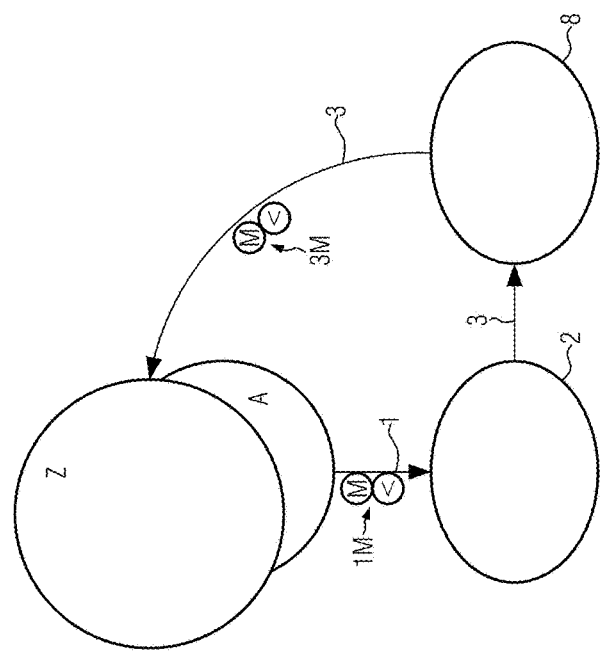
FIG. 2 shows an upgrade of the pasteurization system sketched in FIG. 1.

FIG. 2 shows an upgrade of the design variant that is sketched in FIG. 1. Thereby, identical elements are marked with identical reference signs. In FIG. 2, a sanitation unit 8 is shown for the return flow of the filtered process liquid between the filter unit 2 and the treatment zone Z. The sanitation unit 8 is designed, for example, to add biocide to the process water in a dosed manner. Thanks to this, a sanitation or higher sterilization of the process water may be achieved. It is clear that the addition of biocide may be controlled by a control unit (not shown). The filtered and subsequently sanitized process water is returned to the treatment zone Z, where it may be used again, via a pipeline 3 with a pump 3M.

Figure 3:
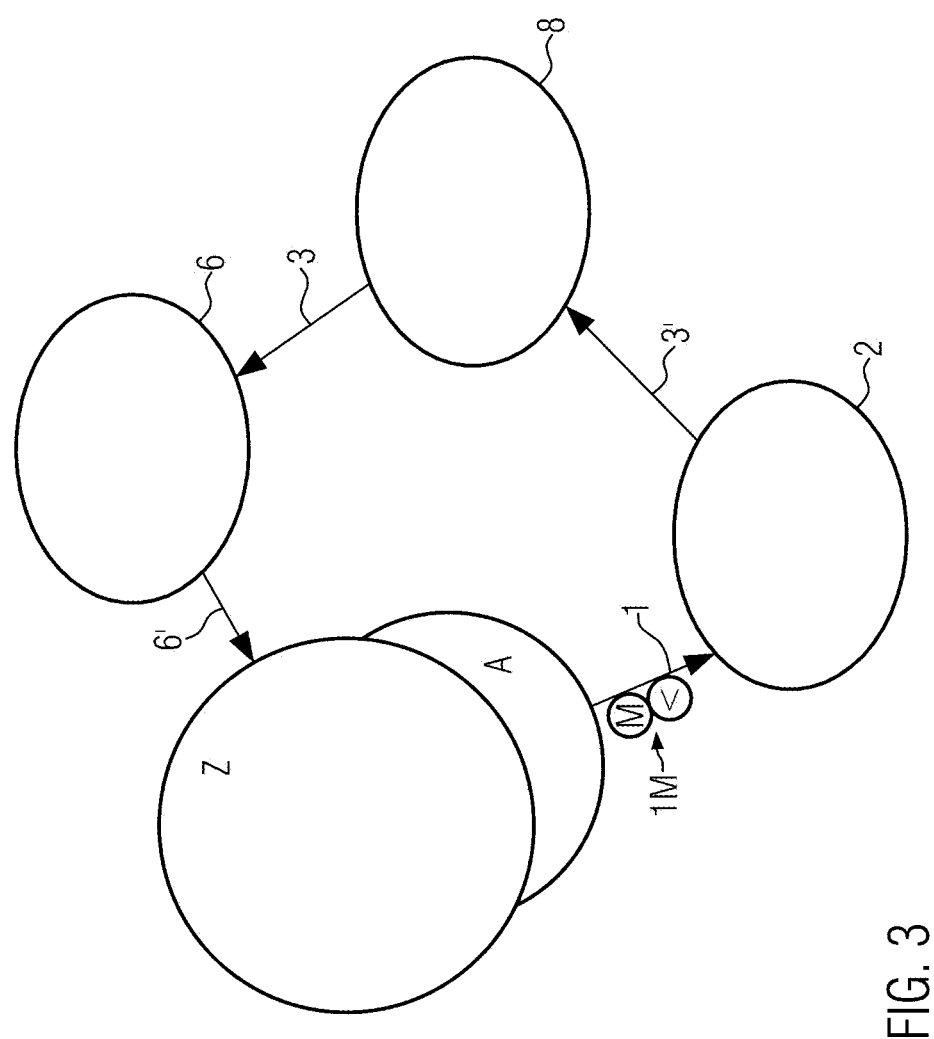
FIG. 3 shows a further upgrade of the pasteurization system shown in the FIGS. 1 and 2.

FIG. 3 shows another upgrade of the design variants from the FIGS. 1 and 2. Thereby, identical elements are again labeled with identical reference signs. FIG. 3 shows all elements of FIG. 2. In addition, FIG. 3 contains an area 3 that designates the internal purification of the pasteurization system. Hence, the area 6 comprises devices that are related to the internal purification of the treatment zone Z of the pasteurization system. In particular, the filtered and purified process water may be used for the internal cleaning process in the area 6. Practically no additional fresh water is consequently needed for the internal cleaning process, but the filtered and sanitized process water may be used. It is clear that, in addition to the elements filter unit 2, sanitation unit 8 and area 6, another filter line that only comprises some of the displayed elements may be installed in parallel (not shown). In particular, a part of the process water may also be used directly for repeated spraying.

FIG. 4 shows another upgrade of the design variant from FIG. 3.

FIG. 4 shows a pasteurization system 100. In a purely exemplary way, the pasteurization system 100 is composed of three sections. The sections comprise: a first section for heating/pre-heating of the containers to be treated through spraying with process water; a second section in which the containers to be treated are cooled down through spraying with process water. As a mere example, each of the sections in FIG. 4 comprises 3 zones. It is clear that each of the sections could also comprise another number of zones. Also, the different sections could comprise a different number of treatment zones. Containers to be treated are typically guided through the zones on at least one conveyor system. FIG. 4 shows two conveyor systems or conveyor belts T1 and T2, which are arranged on top of each other, in an exemplary way. These conveyor belts are driven in an appropriate way in FIG. 4. The engines TM1 and TM2 to drive the respective conveyor belts T1 and T2 are shown in an exemplary way. Hence, containers to be treated may be transported through the treatment zones on two floors or two decks on the conveyor belts T1 and T2.

The first section comprises the zones Z1, Z2, Z3. A heating process of the containers to be treated takes place through spraying. The second section comprises the zones P1, P2, P3. In these zones, the pasteurization is typically implemented with sufficiently warm process water. These zones P1, P2, P3 may also be referred to as pasteurization zones. The zones P1, P2 and P3 are followed in the third section by the zones Z7, Z8 and Z9. In the last three displayed zones, the cooling of the containers, which have previously been treated with warm water, takes place. In the zones Z7, Z8 and Z9, the containers are sprayed with cooler water to cool them down. The zones P1, P2, P3 are typically directly adjacent to the zones Z1, Z2, Z3. This means that the conveyor belts, here T1 and T2, guide the containers to be treated in FIG. 4 from the zones Z1, Z2, Z3 into the zones P1, P2 and P3 and subsequently into the zones Z7, Z8 and Z9. The process water is sprayed from sprinkling systems 15 on the containers. The sprinkling systems 15 are to be installed typically above the containers to be treated and spray the containers essentially from above or obliquely from the side.

Each of the zones Z1, Z2, Z3, P1, P2, P3, Z7, Z8, Z9 shown in FIG. 4 has collector zones with screening units A1, A2, A3, A4, A5, A6, A7, A8, and A9. These screening units are developed in a trough-shaped manner. In these screening units A1, A2, A3, A4, A5, A6, A7, A8, and A9, the process water 17, used in the respective treatment zone Z1, Z2, Z3, P1, P2, P3, Z7, Z8, and Z9, accumulates after use. Through the contact with the containers to be treated, there will be inputs of particles such as glass shards, sand and/or settling sediments in the process water 17. At the same time, organic suspended materials may stick to the containers and partially be detached and subsequently fall into the used process water 17. Due to the humid and warm environment in the treatment zones, especially in the warm treatment zones, biofilms may develop on lateral walls of the respective treatment zones. Parts of these biofilms may detach and fall into the used process water 17 that is collected in the screening units A1, A2, A3, A4, A5, A6, A7, A8, and A9 of the respective treatment zones Z1, Z2, Z3, P1, P2, P3, Z7, Z8, Z9. Inputs of particles, sand and/or settling sediments, that may also comprise organic sediments, sink to the bottom in the screening units of the respective treatment zone. Each of the screening units A1, A2, A3, A4, A5, A6, A7, A8, and A9 respectively comprises screen boxes or collectors 19 at its deepest point to absorb the inputs, i.e. to collect the sediment. Each of the screening containers 19 in the different treatment zones Z1, Z2, Z3, P1, P2, P3, Z7, Z8, Z9 may be filled with sediment to a different extent. The sediment may be removed from the screening container 19 by means of devices to remove the sediment. The devices to remove the sediment may comprise, for example, pumps and valves. FIG. 4 shows valves 1V and at least one pump 1M for the purpose of removing the sediment from the respective screening units and/or their screening container 19. The valves 1V and the (at least single) pump 1M may be individually controlled by a control unit (not shown). Hence, respectively one or, if appropriate, several screening containers may be opened for the removal of sediment and forwarded for the purpose of sediment filtration. The sediment may be removed through a pump 1M which is suitable to develop a vortex flow so that the sediment may be removed from the sedimentation area. In this process, it is clear that a mixture of process water 17 and solid particles, as well as the particles dissolved in the process water 17, may be removed.

The removed process water and sediment are led to a central filter unit 2 through pipes 1. The central filter unit 2 is similar to the central filter unit 2 in the FIGS. 1-3. The central filter unit 2 typically comprises one or several filter modules. A first filter module 11 of the central filter unit 2 is typically a filter module 11 for the filtration of solid matter. This filter module 11 may, as already described based on FIG. 1, comprise a gap filter with a defined gap size. The gap size may, for example, be 40-60 µm. However, other gap sizes are also possible. Therefore, particles with mid-size particle diameters, that are larger than the gap sizes, may be filtered out of the sediment. Consequently, the process water removed from the respective treatment zone is filtered with regard to solid matter, i.e. particles.

In the central filter unit in FIG. 4, a second filter module 4 may be installed in conjunction with the first filter module 11. The second filter module 4 may be configured especially for the filtration of suspended matter and parts of biofilms. Suspended matter, mucilage and usually organic matter floating on and in the water may be removed from the process water to the greatest possible extent by means of this filter module.

In the central filter unit in FIG. 4, a third filter module 5 may follow the first or the second filter module. The third filter module 5 may be designed especially to filter nutrients out of the process water. In the system, the central filter unit may comprise a further filter module that is designed to implement microfiltration and/or ultrafiltration and/or nanofiltration and/or reverse osmosis filtration. Nutrients may suddenly be inputted in the process liquid in a relatively high concentration, for example through leaking or burst containers. The content of leaking or burst containers may blend with the used process water 17 in the screening units of the treatment zones. Membrane filters may be used for this process. Different membrane sizes may remove different types of nutrients from the process water. For example, one or several sub-modules for microfiltration and/or ultrafiltration and/or nanofiltration and/or reverse osmosis filtration may be used in the filter module 5. Thereby, microfiltration comprises an approximate detachable matter size of up to greater than or equal to 0.1 µm for pressure differences of 0.1-2 bar. Ultrafiltration comprises an approximate detachable matter size of up to an order of magnitude lower (i.e. approximately 0.01 µm) than for the microfiltration at pressure differences of 0.1-5 bar. Nanofiltration comprises another order of magnitude lower than ultrafiltration (i.e. approximately up to 0.001 µm) at pressure differences of 3-30 bar. Reverse osmosis filtration is another order of magnitude lower than nanofiltration (i.e. up to approximately 0.0001 µm) at pressure differences of 10-100 bar. Hence, nutrients may be extracted from the process water. As the nutrients existing in the process water may nourish bacteria, biofilms and other organic matter in the process water, filtering the nutrients out may deprive these undesired microorganisms of food.

The central filter unit 2 may comprise a fourth filter module 7 that comprises a UV radiation system to irradiate the process water. Typically, the filter module 7 is to be installed after the filter modules 11, 4 and 5. It may also be installed as a separate unit that is subordinate to the remaining three filter modules. A germicidal effect may be achieved through the UV irradiation. Hence, the UV irradiation may sanitize the pre-filtered process water. Therefore, germs may already be cauterized in the central filter unit. Free radicals, that may have a biocidal effect, may be created through UV radiation. If chemicals or biocidal substances are also added to sanitize the process water (see below), the quantity of the substances to be added may be efficiently reduced through the use of UV irradiation. It is clear that the UV irradiation unit, i.e. the fourth filter module 7, may also be integrated in the central filter unit (not shown in FIG. 4) in a way that a UV irradiation may occur essentially in parallel to the filtration of the process water with one or several or all of the remaining filter modules 11, 4 and 5. Logically, the UV irradiation may be switched on or off in a need-based manner by means of a control unit. After the sediment with process water, removed from the respective screening unit, has passed through the central filter unit 2 with its modules 11, 4, 5 and 7, filtered process water is released by the central filter unit 2. This water may be transferred for further use by means of pumps (not shown).

In the pasteurization system 100 in FIG. 4, a dosage unit 8 is shown after the central filter unit 2. This dosage unit is subordinate to the central filter unit 2. By means of the dosage unit 8, a biocide may be added to the filtered water in a precise dosage. Therefore, the filtered water may be further disinfected on one hand, and the filtered process water may also work as a carrier for the biocide on the other hand. If the process water is re-used, the biocide may be transported to the place where areas within the treatment zones are to be sprayed with the filtered process water, for example with regard to an internal purification, as described in the following, or a rinsing process of pipes. Therefore, the specific dosing of the biocide by the dosage unit 8 may be controlled by means of a control unit.

In the pasteurization system 100 in FIG. 4, the filtered process water is returned to the treatment zones Z1, Z2, Z3, P1, P2, P3, Z7, Z8, and Z9 through pipes. The return flow may thereby be controlled in the respective treatment zones Z1, Z2, Z3, P1, P2, P3, Z7, Z8, and Z9 by means of valves 3V.

In the treatment zones Z1, Z2, Z3, P1, P2, P3, Z7, Z8, and Z9, cleaning units for the internal purification of the respective zones are to be installed. In the example of FIG. 4, cleaning units 6.1 and 6.2 and 6.3 are respectively included in the zones Z1, Z2, Z3, Z7, Z8 and Z9. In the zones P1, P2 and P3, there are only cleaning units 6.2 and 6.3. It is clear that there could possibly also be a different number of cleaning units. The cleaning units 6.1 comprise nozzle systems to spray the ceiling and/or the lateral walls close to the ceiling of the respective treatment zones Z1, Z2, Z3, Z7, Z8 and Z9. The cleaning units 6.1 shall typically be installed above the sprinkling nozzles 15.

The filtered process water, that typically contains biocide, may consequently reach ceiling areas of the respective treatment area, which are mostly shaded in the normal spraying mode; i.e. although liquid and heat may enter these areas, they may be reached only hardly by process water from the sprinkling nozzles 15.

Rotating nozzles that are rotatable by 360° may, for example, be used as a nozzle system for the purification spraying process. Hence, practically all areas above the sprinkling nozzles 15 may be cleaned. The process water used in the cleaning process, as well as the dirt particles or biofilm parts detached by or included in this process water, are returned to the screening units A1, A2, A3, A4, A5, A6, A7, A8, and A9, and may in turn be transferred to the central filter unit 2 by pulling off the appropriate sections.

The cleaning units 6.2 are to be installed between the conveyor systems T1 and T2 and may rinse the lateral walls or the bottom sides of the conveyor systems T1 and T2 there.

Hence, lateral areas or bottom sides, which are hardly sprayed with process water in the sprinkling mode, may be sprayed and hence cleaned by means of the cleaning units 6.2. The cleaning units 6.2 may be provided with filtered process water at the same time or, if appropriate, separately by the cleaning units 6.1. Similar to the cleaning units 6.1, the cleaning units 6.2 may use rotating nozzles, that are rotatable by 360°, so that practically all areas between the two conveyor systems T1 and T2 may be sprayed by means of the rotating nozzles. It is clear that in a unit, in which there is only one conveyor system (not shown here), a cleaning unit equal to the cleaning unit 6.2 may typically be installed under the conveyor system.

In the treatment zones Z1, Z2, Z3, P1, P2, P3, Z7, Z8, and Z9, cleaning units 6.3 are to be installed in the area of the screening units A1, A2, A3, A4, A5, A6, A7, A8 and A9. The cleaning units 6.3 have the special characteristic of being installed in an area that is located under the water level 17A of the process liquid 17 in the respective treatment zone in the normal sprinkling mode. The process water 17 from a treatment zone may though be evacuated. Through the pipe 9, the collected, used process water 17 may be evacuated in FIG. 4 from one or several or all screening units A1, A2, A3, A7, A8 and A9, that essentially collect cold, used process water 17. Similarly, the collected, used process water 17 may be evacuated via the pipe 10 from one or several or all screening units A4, A5 and A6 which essentially collect warm process water 17. A screening unit that is subsequently emptied may then also be rinsed by means of a nozzle unit 6.3 so that areas in the respective treatment zone, that are normally located under the water level, may be cleaned. Hence, the hygiene in the respective treatment zone may be further improved.

By means of a central control unit (not shown), the internal purification of the respective treatment zones may be controlled in an automated way. The internal purification may practically occur automatically during operation of the pasteurization system if the following aspects are taken into account. During operation of the system, "a gap" may be created. This means that no bottles or containers stand on the conveyor belts for a certain time that corresponds to a certain spatial width while the conveyor speed is kept constant. For example, this spatial width may comprise the width of one to two widths of one of the treatment zones. Such a gap may also emerge if a so-called product change occurs. This means that the system switches from spraying of one container type to another container type. The gap is taken advantage of in a way that in the treatment zone, in which no containers are being sprayed for the time being and which corresponds to the gap, the internal purification of the treatment zone may be implemented. A control unit may control the internal purification. This means especially the switch to internal purification and the switch back to the sprinkling mode for the respective treatment zone. Therefore, an internal purification of a treatment zone may practically be implemented in a fully automated way during operation.

Furthermore, the central control unit may control to which of the treatment zones Z1, Z2, Z3, P1, P2, P3, Z7, Z8, and Z9 the filtered process water is returned. The central control unit may be designed especially in a way to use warm, filtered process water from warm zones, for example from the zones P1, P2 or P3, for the internal purification of the colder zones Z1, Z2, Z3, Z7, Z8, and Z9.

FIG. 4 further shows pipes 13 with pumps 13M for each of the treatment zones Z1, Z2, Z3, P1, P2, P3, Z7, Z8, and Z9 with their respective screening units A1, A2, A3, A4, A5, A6, A7, A8 and A9, that may pump collected process water 17 directly to the sprinkling nozzles 15. In the screening unit, solid matter and particles typically sink to the deepest point in the collector containers 19. An extraction of process water 17 above these points may ensure that process water, from which the particles have already sunken down, will be re-used, i.e. water that is less contaminated with particles. An upgrade of this aspect is shown in FIG. 5.

Figure 5:
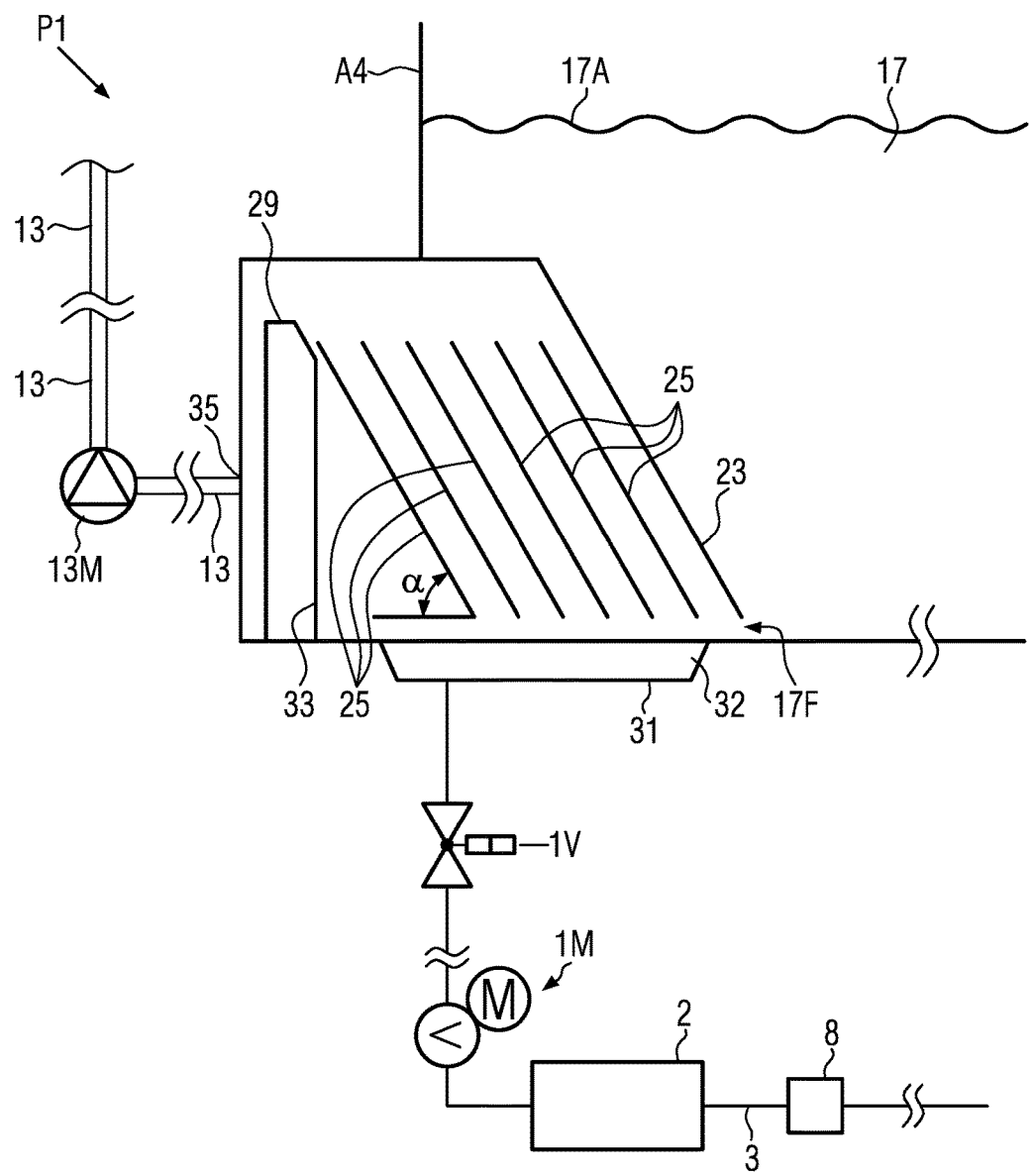
FIG. 5 shows a section of the pasteurization system from FIG. 4 in which an inclined blade purifier is to be installed in addition.

FIG. 5 shows, based on the example of a treatment zone that may correspond to each of the treatment zones Z1, Z2, Z3, P1, P2, P3, Z7, Z8, and Z9 illustrated in FIG. 4, an upgrade for the screening units A1, A2, A3, A4, A5, A6, A7, A8 and A9. The zone P1 with the pertaining screening unit A4 is shown in a purely exemplary manner. There is used process water 17 in the screening unit A4. A water line 17A of the collected, used process liquid 17 is shown. Sediment 32 is collected in a collector container 31 that may be identical to the collector 19 from FIG. 4. As already explained by means of FIG. 4, this sediment is fed into the central filter unit 2 through a valve 1V and by means of a pump 1M. The central filter unit 2 is identical to the central filter unit shown in FIG. 4. The individual filter modules of the central filter unit 2 are not shown in FIG. 5. However, it should be evident that the same filter modules are to be included also in FIG. 5. The filtered process water is led through a pipe 3 to the dosage unit 8 where it may be further used, especially for the internal purification of the treatment zones; see FIG. 4.

FIG. 5 further shows an inclined blade purifier that is meant to purify process water 17 from the screening unit A4 before it may be used directly for another spraying process. FIG. 5 contains a partition wall 23 of the screening unit A4 that does not fully extend up to the bottom of the screening unit A4. The arrow 17F indicates a flow direction or current direction of the collected, used process liquid 17. This flow 17F of the process liquid 17 may be created by means of a pump 13M. The use of a suction device or a combined pumping and suction device (not shown) is also possible. FIG. 5 shows several inclined blades 25 that are arranged in parallel to each other. The distance between the blades 25 is typically constant. However, it is also possible to choose different distances or to place groups of blades 25 at different distances from each other. FIG. 5 shows six blades 25 in a merely exemplary way. However, it is clear that another number of blades could also be chosen. The collected process liquid 17 flows alongside the blades 25. Through an overflow edge 29, the process liquid 17 flows to the pump 13M. The process liquid 17 flowed over the overflow edge may leave the screening unit A4 again at the aperture 35. From the aperture 35, the process liquid may flow through the pipe 13 to the pump 13M and back to a treatment zone of the pasteurization system 100 from there; see FIG. 4. The overflow edge 29 is shown in a purely exemplary manner above the end of the blades 25. However, it is equally possible to choose the upper level of the overflow edge 29 in a way as to fit the upper edges of the blades 25. The blades 25 typically have the same size/dimensions. In FIG. 5, the blades 25 are installed respectively at the same altitude. This means that the lower and the upper end of each blade have the same distance in relation to the bottom of the screening unit A4. A partition edge 33 shall be included on the left of the blades 25, which may separate, together with the overflow edge 29, the blades 25 from the gap of the screening unit 1, i.e. the aperture 35. The blades 25 shown in FIG. 5 are to be installed at an angle $\alpha$ in relation to the horizontal plane. The angle $\alpha$ may, for example, be $30°<\alpha<60°$ to support the sedimentation of the particles 32 under the effect of gravity alongside the surfaces of the blades 25. Hence, a more effective treatment, i.e. purity of the process water to be re-used, may be achieved.

The design variants shown in the FIGS. 1-5 may reduce operating costs based on water, electricity and working hours, that arise as a consequence of the forced production downtime for thermal sanitation and manual cleaning of the system. Process water may be reused, both for internal purification as well as for the spraying process. Hence, maintenance intervals may be extended or even omitted completely in some cases.

The invention claimed is:

1. A pasteurization system with purification of a process liquid with at least one feed and
   an evacuation conveyor system for containers, comprising:
   a plurality of treatment zones with sprinkling nozzles to spray the containers with the process liquid, each of the plurality of treatment zones includes a screening unit with a sedimentation area for deposition of sediment from the process liquid;
   a closed-loop circuit to re-use the process liquid;
   a separate central filter unit;
   one or more devices for removal of the sediment from the sedimentation areas of each of the plurality of treatment zones and for feeding of the sediment removed from the sedimentation area of each of the plurality of treatment zones into said separate central filter unit;
   the separate central filter unit having at least one filer module to filter solid matter out of the sediment that is fed into the separate central filter unit, so that filtered process liquid is obtained; and
   one or more further devices to return the filtered process liquid to one or more of the plurality of treatment zones.

2. The pasteurization system according to claim 1, the one or more devices for removal of the sediment from the sedimentation areas of each of the plurality of treatment zones are designed to develop a vortex flow in a way that removes the sediment form the sedimentation area.

3. The pasteurization system according to claim 1, the separate central filter unit including a further filter module for filtration of suspended sediments.

4. The pasteurization system according to claim 1, the separate central filter unit including another filter module designed to implement at least one of microfiltration, ultrafiltration, nanofiltration, or reverse osmosis filtration.

5. The pasteurization system according claim 1, the separate central filter unit including another filter module to irradiate the filtered process liquid with UV radiation.

6. The pasteurization system according to claim 1, the separate system including a dosage unit designed to add biocide to the process liquid filtered by the central filter unit.

7. The pasteurization system according to claim 1, one or several or all of the plurality of treatment zones each comprise an internal purification module with one or several nozzle systems which are designed to clean one or several internal areas of the plurality of treatment zones with the filtered process liquid.

8. The pasteurization system according to claim 7, at least one of the nozzle systems designed to spray a ceiling above the sprinkling nozzles with the filtered process liquid.

9. The pasteurization system according to claim 7, the containers to be sprayed in the plurality of treatment zones being guided on several feed and evacuation conveyor systems of the at least one feed and evacuation conveyor systems arranged on top of each other in a way that areas located between said several feed and evacuation conveyor systems can be cleaned.

10. The pasteurization system according to claim 9, at least one of the nozzle systems being arranged in a way that areas that are located underneath water level during operation can be rinsed.

11. The pasteurization system according to claim 10, the nozzle systems having rotational nozzles that are 360° rotatable.

12. The pasteurization system according to claim 11, in combination with a control unit designed to control devices for removal of the sediment from the sedimentation area for each of the plurality of treatment zones and for feeding the sediment into the separate central filter unit.

13. The pasteurization system according claim 12, the control unit being designed to measure the temperature of the process liquid of at least two treatment zones of the plurality of treatment zones, respectively, and designed to use the filtered process liquid from one treatment zone of the at least two treatment zones of the plurality of treatment zones for internal purification of another treatment zone of the at least two treatment zones of the plurality of treatment zones, said one treatment of the at least two treatment zones of the plurality of treatment zones having a higher measured temperature of the process liquid than the another treatment zone of the at least two treatment zone of the plurality of treatment zones.

14. The pasteurization system according claim 13, the screening unit of each of the plurality of treatment zones comprising a pump and an inclined blade purifier, arranged under a surface of the process liquid, with several parallel, inclined blades, the pump provided to pump the process liquid alongside the blades.

15. The pasteurization system according to claim 14, the pump provided to pump the process liquid over a deepest point of each respective treatment zone from the plurality of treatment zones so that the sediment can be deposited into the sedimentation area.

* * * * *